United States Patent [19]

Tofighi et al.

[11] Patent Number: 5,795,330

[45] Date of Patent: Aug. 18, 1998

[54] MIXING DEVICE

[75] Inventors: Aliassghar Tofighi, Belmont, Mass.; Alfred V. Vasconcellos, Cranston, R.I.; Katherine Jacobs, Sagamore Beach; Pramod Chakravarthy, Cambridge, both of Mass.

[73] Assignee: Etex Corporation, Cambridge, Mass.

[21] Appl. No.: 728,440

[22] Filed: Oct. 10, 1996

[51] Int. Cl.$^6$ .................................................. A61M 37/00
[52] U.S. Cl. ...................................... 604/82; 604/37
[58] Field of Search .................................. 604/82, 37, 56, 604/57, 83, 84, 85, 92, 142, 257; 222/420

[56] References Cited

U.S. PATENT DOCUMENTS

| | | | |
|---|---|---|---|
| 1,004,103 | 9/1911 | Tacey | 604/83 |
| 2,112,581 | 3/1938 | Tacey | 604/83 |
| 4,950,237 | 8/1990 | Henault et al. | 604/82 |
| 5,435,645 | 7/1995 | Faccioli et al. | |

FOREIGN PATENT DOCUMENTS 2838222  3/1991  Germany.

OTHER PUBLICATIONS

Thomas Register 1994, Adhesives, p. 254.

*Primary Examiner*—Wynn Wood Coggins
*Assistant Examiner*—Nikent Gring
*Attorney, Agent, or Firm*—Clark & Elbing LLP

[57] ABSTRACT

A mixer for the mixing of a first and a second component, comprising a flexible pouch which contains said first component and which has an inner surface that is non-retaining to the components; means for supplying the second component to the chamber for mixing with the first component; and a neck attached to said pouch.

23 Claims, 3 Drawing Sheets

MIXING DEVICE

BACKGROUND OF THE INVENTION

The field of the invention is containers for shipping, storing, and activating biologically active powders. One such powder is bioceramic precursor powder which is mixed with a liquid to form a paste which is inserted where needed to make synthetic bone.

SUMMARY OF THE INVENTION

The invention features a mixer for mixing a first and a second component. The mixer includes a flexible pouch which contains the first component and which has an inner surface that is non-retaining (as hereinafter defined) to the components. The mixer also includes means for supplying the second component to the chamber for mixing with the first component, and a neck which is attached to the pouch for removing the mixed components following mixing. In a preferred embodiment, the first component is a medical useful substance, e.g., a bioceramic precursor powder, and the second component is a liquid which is mixed with the powder to form a synthetic bone paste.

In one preferred embodiment, the material making up the pouch and neck is an elastic material. Alternately, the pouch and neck may be made of a non-elastic material. The neck may be closed with a rubber stopper or with a valve. The neck may be made of a material that may be cut with, for example, scissors to squeeze out the paste after mixing. The neck may also have a valve through which the paste flows. In another embodiment, the neck may include multiple compartments to facilitate mixing in stages. In another embodiment, the neck may be connected to multiple pouches. In another embodiment, a venting apparatus may be included.

The invention facilitates complete mixing of a powder and a liquid. The single piece construction of the device means that there are no seams or corners in the pouch where unmixed material might otherwise be trapped. Another advantage of the mixer of the invention is that it is inexpensive to produce, which is especially advantageous in light of the fact that it is intended to be disposable.

Other features and advantages of the invention will be apparent from the following description of the preferred embodiments thereof, and from the claims.

DETAILED DESCRIPTION

Structure

Figure 1:
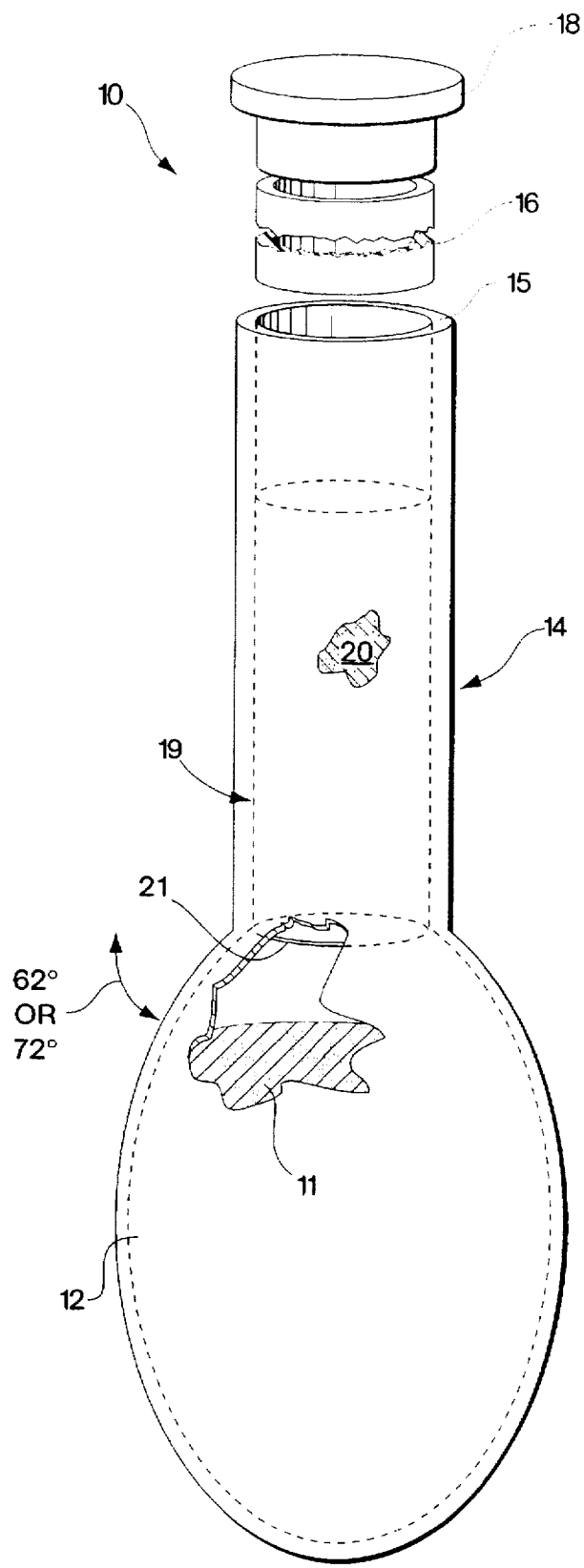
FIG. 1 is a plan view of a mixer of the invention.
Figure 2:
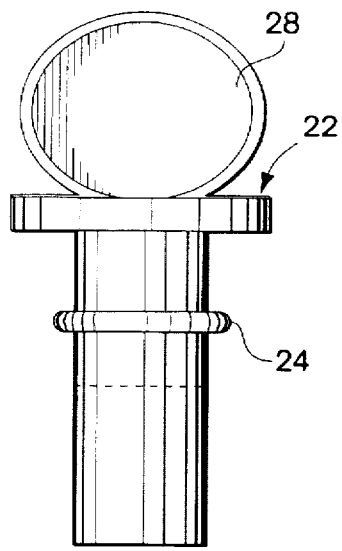
FIGS. 2, 3, and 4 are, respectively, front, side, and perspective views of a stopper for the neck of the mixer, showing the protecting member.
Figure 3:
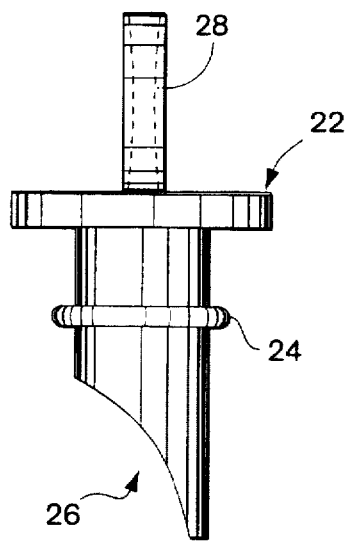
Figure 4:
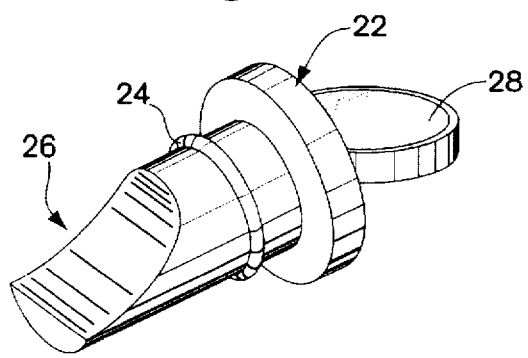

FIG. 1 illustrates a preferred embodiment of a mixer 10. Bioceramic precursor powder 11 is held inside a pouch 12 which is formed of one piece of flexible elastic material, which might be, for example, polyurethane, silicone, Krayton, polyethylene, rubber latex, or another elastomer. Neck 14, with mouth 15, is formed of the same piece of material as pouch 12. Pouch 12 and neck 14 are formed so as to have no seams which might hinder the uniform mixing of powder 11. A protective insert 16 made, for example, of polypropylene tubing, may be used to reinforce neck 14. A stopper 18, preferably made of rubber, closes the mouth 15. The dimensions of mixer 10 are: height of pouch 11: 4.5 cm; height of neck 14: 4.5 cm; width of pouch: 0.3 cm; volume of pouch, not including neck: 15 ml. Alternative measurements are: height of pouch: 3.4 cm; height of neck: 3.4 cm; width of pouch: 1.3 cm; volume of pouch: 5 ml.

Manufacture

There are several ways to manufacture mixer 10 using known container manufacturing techniques. For example, the mixer can be injection molded, dipping molded, rotational molded, or blow molded. All of these methods are conventional and well-known and need not be described herein.

The pouch 12 should be made of a flexible material. In some instances, the pouch should be flexible enough to be compressed by hand. In other embodiments, where mixing is carried out by a mechanical or other non-manual approach, a more rigid (although still somewhat flexible) material may be employed.

The neck 14 may be manufactured to be continuous with pouch 12, or may be affixed separately. Any form of attachment may be used as long as it does not tend to trap components to be mixed or adversely interfere with the entry or evacuation of components into or out of the pouch 12. Manufacture of additional features such as protective inserts, caps, ports, valves etc. will be guided by considerations known in the art.

The mixer of the invention allows for the storage, shipping, combining and mixing of components without the need for opening the package prior to mixing. Thus the invention is particularly well suited for the shipment of sterile powders for sterile reconstitution with liquids or sterile mixing with other powders without the risk of contamination.

The mixing pouch serves as a reservoir for combining components to be mixed. The neck permits introduction of components to be mixed, as well as adding space to allow incorporation of additional useful features such as caps, plugs, labels, handles, vents, attachments, and the like. The sealed mixer may be sterilized if required.

In preferred embodiments, the pouch has a capacity on the order of 1 to 20 mls, and allows convenient manual mixing of components contained therein. In smaller sizes (less than 10 mls) mixing is accomplished by kneading, pinching, or squeezing the flexible pouch with the thumb and forefinger of one hand. In larger sizes, the fingers of both hands may be employed simultaneously, or other methods such as use of a fist or palm of the hand may also be effective.

The neck may be of any useful length and does not generally participate in the mixing function, but rather provides a means for the storage of additional components, means for introducing components to be mixed, means for evacuating the pouch following mixing, and space to add additional useful features such as caps, labels, handles, injection ports, vents, attachments and the like.

The requirements as to the materials used in manufacturing the neck, or the means of attachment to the pouch will be dictated by the intended functionality of the neck. The neck may be manufactured continuously with the pouch as a single entity, or may be attached to the pouch by any suitable means such as but not limited to a connector attached to the pouch by glue, compression fitting, friction fitting, or threads. The connector may be a distinct piece or continous with either the pouch or the neck.

The means for introducing additional components to the pouch will most often be present in the neck or specific attachments thereto. While it is possible for introducer means to exist on the pouch itself (e.g., a syringe needle penetrable pouch material, or the use of a gas or liquid permeable or semi-permeable pouch), in most cases this will be avoided because the presence of the introducer means can deleteriously affect the non-retaining character of the pouch inner surface.

Figure 5:
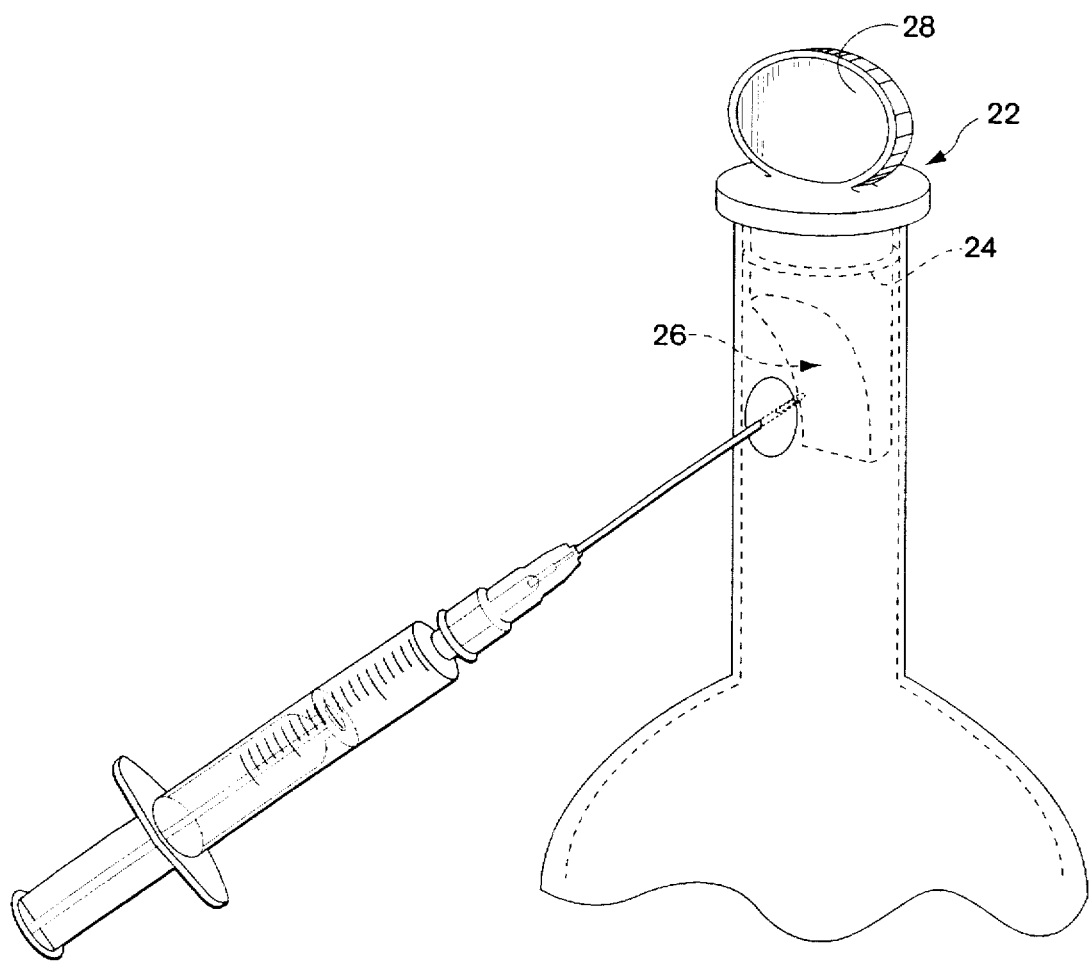
FIG. 5 is a side view of the pouch of the invention, with a syringe, showing the inside protecting member.

Any number of components may be introduced into the pouch provided their total volume does not exceed the volume of the pouch itself. Likewise, any introducer means appropriate for supplying the material to be mixed to the pouch may be employed. Suitable introducer means include but are not limited to valves, ports, permeable or semi-permeable membranes, needle septa and the like. In one preferred embodiment, where a substance is introduced via a syringe needle through the upper portion of the neck, a specialized stopper is used. The stopper limits the possibility of an accidental needle stick to the user by preventing unintended passage of the needle entirely through the neck. The specialized stopper, shown in FIG. 5, features a protecting member, generally flat, which extends into the neck. The needle is introduced into the neck at a point above the lower extent of the protecting member.

In the mixing process, two functions must occur: the movement of the pouch material in opposition to itself should be easily performed, in most cases by hand, and there must be no structures or features within or on the inner surface of the pouch which would tend to trap one or more of the components to be mixed or otherwise deleteriously affect the mixing process and result in incomplete mixing. Since the pouch is flexible, these same considerations apply to the outer topography of the pouch, as they can affect the shape of the pouch inner surface during the mixing process. Likewise, the features of the inner pouch surface should not significantly hinder the evacuation of the mixed components or reaction products therefrom. Pouch designs meeting the above criteria are said to have non-retaining inner surfaces.

The requirements regarding the surface topography and geometry to produce a non-retaining surface can vary, depending on the type of components to be mixed. For example, in the case of dry powders, preferred pouches will be smooth and free of entrapping edges, pits, corners, or seams. In other embodiments, one or more of these potentially entrapping features may be present, provided their dimensions are significantly smaller than the grain or particulate size of the powder. Thus mixing of powders with a minimum particle size of 100 µm diameter would not be adversely affected by the presence of 1 µm diameter pits or 1 µm high edges. In the case of the mixing of low viscosity liquids or gases, edges may be tolerated provided they are not so severe as to hinder pouch movement during mixing or hinder the evacuation process.

Following completion of the mixing process the mixed components (or reaction products or combination thereof) may be stored within the pouch. The contents of the pouch may then be removed from the pouch by opening the pouch using cutting instruments or the like. In some embodiments the mixer may be opened at the neck either by cutting the neck or otherwise providing an opening (e.g. by removing a cap or plug) and the contents removed through the use of an implement such as a syringe, pipette or spatula. In preferred embodiments the components are extruded through the neck. In this regard, the flexible nature of the pouch facilitates extrusion of the components, since it may be squeezed or rolled like a toothpaste tube.

Referring to FIG. 1, in mixer 10, the neck includes a reservoir 19 containing a component 20 to be mixed with a second component 11 within the pouch. The frangible seal 21 between the storage compartment and the pouch insures separation of the components during shipping and storage. Component 20 is introduced into the pouch by breaking the frangible seal 21, and transferring component 20 into the pouch, where mixing is carried out.

In one embodiment, a mixer of the invention is used as a package for shipping, storing, and mixing a bioceramic precursor powder for use as a surgical synthetic bone replacement material which is stored in powder form and mixed with a liquid immediately before use to form a paste. Many bioceramic precursor powders are known, e.g., those disclosed in U.S. Pat. No. 5,178,845, hereby incorporated by reference.

The mixer is shipped from manufacturer to medical center in the form of a kit which includes a sterile pre-filled syringe and needle containing sterile water or buffer. The mixer is sealed and sterile, and contains the bioceramic precursor powder. The kit also optionally includes a spatula and/or syringe for the application of the paste by the user, and an optional portable mechanical mixer.

Referring now to FIGS. 2, 3, 4, and 5, a preferred stopper for insertion into the neck of the mixer is shown, including head 22, lip 24, and injection site 26 and handling means 28. Water is added to the mixer by insertion of a needle into the upper neck region; the protective member protects the user from accidentally inserting the needle entirely through the device and causing injury to himself.

The mixer and powder are stored in a medical facility until needed. When there is a surgical procedure where synthetic bone is needed, liquid is injected into the pouch through the neck above the end of the protective member present on the stopper and the powder-liquid mixture is mixed by hand while still inside the pouch. When the components are mixed sufficiently to form a paste, the neck is cut, and the paste is squeezed out of the pouch into a syringe or a petri dish, depending on the surgical requirements. The mixer is discarded after extrusion of the paste.

Alternate Embodiments

There are several alternate embodiments possible for various components of the mixer.

In one embodiment, reproducible and highly controlled mixing of the components within the mixer is obtained through the use of a mechanical mixer adapted to accept the flexible pouch and to mix the components therein.

In the general construction of the mixer, multiple bulbs may be joined at the neck to allow discrete mixing steps. Mixtures in different bulbs can then later be combined. The mixer can be used to mix not just bone paste, but a variety of materials. The mixer is not limited to holding a powder, but can be used to mix liquids, pastes, powders, or combinations. The mixer may also include venting means for gases produced by chemical reactions of mixed components.

Preferably, the material of the pouch is elastic, but it can also be made of a non-elastic material, such as polyethylene films.

Several designs are possible for the neck. The neck generally performs two functions, supplying the liquid to the pouch and ejecting the mixture from the pouch. In the preferred embodiment, liquid is supplied to the pouch with a syringe through a rubber stopper. Alternately, there may be a valve to allow liquid to pass into the pouch.

For ejecting the liquid, more than one option is possible. In the preferred embodiment, the neck is cut with scissors, and the surgeon squeezes the mixture out of the pouch. Alternatively, the neck may be fitted with a valve to squeeze the mixture out.

The neck can be reinforced with a protective insert, and/or fitted with a handle to facilitate holding the mixer. The neck may include several compartments which can be breached to introduce their contents into the pouch.

What is claimed is:

1. A mixer for the mixing of a first and a second component, comprising:
   a) a flexible mixing pouch which in use contains the first component and which has a continuous inner surface that is non-retaining to the components, wherein a portion of the inner surface opposably contacts another portion during mixing; and
   b) means for supplying the second component to said pouch for mixing with the first component, said supplying means comprising a needle port, needle penetrable material, or a valve through which a second component can be introduced into said mixing pouch.

2. The mixer of claim 1 wherein said means for supplying said second component comprises a neck attached to said pouch.

3. The mixer of claim 2 wherein said neck further comprises a cap.

4. The mixer of claim 3 wherein said cap includes a protecting member and handling means.

5. The mixer of claim 2 wherein said pouch and said neck are formed of an elastic material.

6. The mixer of claim 2 wherein the said pouch and said neck are formed of a non-elastic material.

7. The mixer of claim 2 wherein the said neck is adapted to be removable from said pouch.

8. The mixer of claim 2 further comprising a valve in the neck through which the mixture can be ejected.

9. A mixer of claim 8, wherein said valve is also adapted for introducing a second component into said mixing pouch.

10. The mixer of claim 2, further comprising a venting apparatus attached to said neck.

11. The mixer of claim 2, further comprising multiple pouches joined at the neck.

12. A mixer of claim 2, further comprising a valve in said neck through which a second component can be introduced into said mixing pouch.

13. The mixer of claim 1, wherein the mixer is adapted to be used with a mechanical mixing device.

14. A mixer of claim 1 having a single neck configured for the addition of liquid to the pouch and for the removal of material from the pouch.

15. A mixer of claim 1, wherein said first component includes a powder.

16. The mixer of claim 2 wherein said supplying means comprises a needle port or needle penetrable material.

17. The mixer of claim 2, further comprising a stopper to close the mouth of said neck.

18. The mixer of claim 2 wherein said first component contained within said pouch is a medically useful substance, and said second component is a liquid.

19. The mixer of claim 8 wherein said first component is a bioceramic precursor powder.

20. A method for preparing a medically useful composition, said method comprising the steps of:
    a) providing the mixer of claim 6 wherein said first and second components are in sterile form;
    b) introducing said liquid through the supplying means;
    c) mixing the combined components in said pouch; and
    d) removing the components from the pouch.

21. A kit comprising:
    a) the mixer of claim 18 wherein said first component is in sterile form; and
    b) a syringe containing said second component in sterile form.

22. The kit of claim 21, further comprising means for application of said mixed components to a mammal.

23. The kit of claim 22, wherein said application means comprises a spatula or a syringe.

* * * * *